United States Patent [19]

Mims

[11] Patent Number: 4,701,188
[45] Date of Patent: Oct. 20, 1987

[54] NATURAL GAS CONDITIONING SYSTEM AND METHOD

[75] Inventor: Charles R. Mims, Sumrall, Miss.

[73] Assignee: Mark Industries, Inc., Palo Alto, Calif.

[21] Appl. No.: 638,554

[22] Filed: Aug. 7, 1984

[51] Int. Cl.⁴ ............................................. B01D 47/10
[52] U.S. Cl. ............................................. 55/20; 55/31; 55/32; 55/48; 55/160; 55/208; 55/222; 55/234
[58] Field of Search ............................... 55/20, 29–32, 55/48, 160, 185, 208, 217, 222, 223, 233, 234, 259

[56] References Cited

U.S. PATENT DOCUMENTS

| | | | |
|---|---|---|---|
| Re. 25,759 | 4/1965 | Walker et al. | 55/160 X |
| 1,827,092 | 10/1931 | Martocello | 55/222 |
| 2,690,814 | 10/1954 | Reid | 55/32 |
| 2,812,827 | 11/1957 | Worley et al. | 55/32 |
| 2,812,830 | 11/1957 | Sattler et al. | 55/31 |
| 3,104,958 | 9/1963 | Smith et al. | 55/48 X |
| 3,119,674 | 1/1964 | Glasgow et al. | 55/32 X |
| 3,212,238 | 10/1965 | Welch et al. | 55/31 X |
| 3,288,448 | 11/1966 | Patterson et al. | 55/32 X |
| 3,318,071 | 5/1967 | Sinex | 55/160 X |
| 3,331,188 | 7/1967 | Sinex | 55/31 |
| 3,367,089 | 2/1968 | Scott | 55/31 X |
| 3,405,509 | 10/1968 | Coggins | 55/160 |
| 3,541,763 | 11/1970 | Heath | 55/31 X |
| 3,768,234 | 10/1973 | Hardison | 55/223 |
| 3,793,809 | 2/1974 | Tomany et al. | 55/223 X |
| 3,881,898 | 5/1975 | Darby et al. | 55/223 X |
| 3,907,526 | 9/1975 | Saleern et al. | 55/236 |
| 3,944,402 | 3/1976 | Cheremisinoff | 55/223 X |
| 4,070,165 | 1/1978 | Colton | 55/30 |
| 4,164,399 | 8/1979 | Kannapell | 55/223 |
| 4,300,913 | 11/1981 | Egert et al. | 55/223 X |
| 4,432,779 | 2/1984 | Honerkamp et al. | 55/223 |

Primary Examiner—Robert Spitzer
Attorney, Agent, or Firm—Cushman, Darby & Cushman

[57] ABSTRACT

A natural gas separation and dehydration system includes a separation stage wherein the gas is expanded to effect removal of liquid water and liquid hydrocarbons. The flow of raw gas to the separation stage may be directly from the well or via a heat exchanger in which the gas is heated by heat exchange with hot glycol, the flow being controlled in response to the temperature in the separation stage so as to maintain a desired temperature range in the latter. The gas flows from the separation stage to a dehydrator stage of special construction wherein the gas flows in both co-current and counter-current relationship with glycol.

11 Claims, 4 Drawing Figures

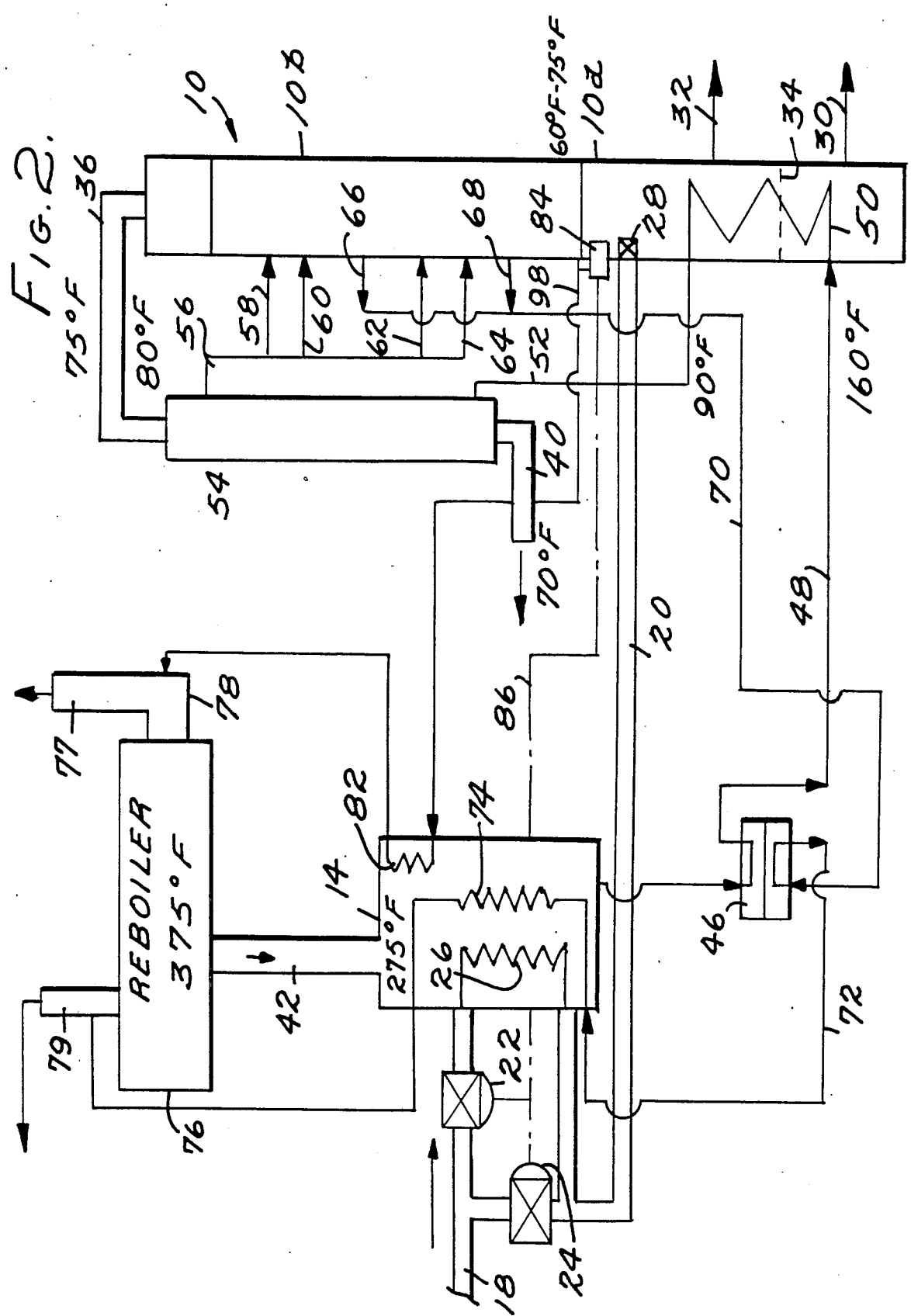

NATURAL GAS CONDITIONING SYSTEM AND METHOD

This invention relates to the conditioning of natural gas at a gas well site and in particular to conditioning equipment for removing liquid waste and condensible hydrocarbons and for absorbing water vapor from the gas into a liquid dessicant.

BACKGROUND

Natural gas flowing from natural gas wells typically contains water vapor, condensible hydrocarbons and entrained liquids such as water droplets and oil droplets. It is common practice to condition the natural gas at a wellhead to remove these materials from the gas before it passes into the gas pipeline leading from the well. Such removal is necessary in order to prevent clogging of pipelines with liquid water and liquid hydrocarbons which separate as a result of the lower temperatures existing in the transport system, to prevent formation of hydrates which also can clog the system and to prevent corrosion of pipelines, tanks and other components of the system. The principles of such conditioning operations are well known. Water droplets are frequently removed by any of a vareity of mechanical gas-liquid separators. Condensible hydrocarbons and additional water are generally removed by expanding the high pressure well gas so that the resulting temperature drop causes condensation of the condensibles, the condensed liquids being readily separated from the non-condensed gas. Subsequent dehydration of the gas is most commonly achieved by contacting it with a hygroscopic liquid, i.e. a liquid dessicant or absorbent such as diethylene and triethylene glycol whereupon the water vapor is absorbed into the liquid dessicant. The dessicant is then regenerated by heating it to drive off water, and the resulting concentrated dessicant is recycled to the dehydration step. The heat required for regeneration is obtained by burning a portion of the natural gas.

Two of the essential pieces of equipment used for natural gas conditioning are a separator and a dehydrator, the former removing entrained liquids and condensibles and the latter removing water vapor. These are often separate pieces of equipment, but they may be combined in a single separator-dehydrator unit. The separator unit or separator section of a combined unit includes an expansion valve or choke for the natural gas and typically a stratification type water-hydrocarbon separator. The dehydrator unit or the dehydration section of a separator-dehydrator unit is in principle a gas-liquid contact tower in which the wet gas is brought into intimate contact with strong glycol. The regenerator or reboiler is a separate unit usually in the form of a distillation column or the equivalent.

Examples of systems for conditioning raw natural gas a the well site, to remove liquid components, condensibles and water vapor are described in a number of U.S. patents including U.S. Pat. Nos. 2,690,814, 2,812,827, 2,812,830, 3,212,238, 3,331,188, 3,367,089, 3,541,763 and 4,070,165.

SUMMARY OF THE INVENTION

The general overall object of the present invention is to provide a separator-dehydration-reboiler system which is an improvement over prior systems in terms of its efficiency of operation, reduced hook-up costs and reduced space requirements (so that the system can be mounted on a relatively small skid).

Several features contribute to the increased efficiency of operation, one of whiich is the heating of the raw natural gas, prior to expansion and when necessary, by heat exchange with hot glycol from the glycol reboiler. This aspect of the invention eliminates the use of a gas-fired line heater for the raw natural gas, thereby reducing energy consumption by a substantial amount. It also provides control of the heating operation such that a desired temperature or temperature range is maintained in the separator where expansion of the gas takes place. In the preferred construction a bypass valve arrangement provides that the raw well gas can bypass the heat exchanger and flow directly to the separator without being heated or can flow partially or wholly through the heat exchanger. A temperature sensor at the separator senses the temperature of the expanding gas and controls the bypass valve arrangement, i.e. the degree of heating of the gas, such that the desired temperature exists in the separator. The temperature in the separator is an important process parameter, because if the temperature is too low, freezing may occur and if the temperature is too high there is reduced recovery of condensible hydrocarbons. Carry over of the latter from the separator has an adverse effect on the subsequent dehydration operation and on the quality of the gas passing to sales. Typically a temperature range of about 60° F. to about 75° F. in the separator is desirable. Accordingly, if the separator temperature rises to above about 70° F., the control assembly causes the well gas to bypass the heat exchanger; if the separator temperature falls to less than about 60° F., the control assembly causes some or all of the well gas to pass through the heat exchanger.

A further contribution to the efficient operation of the system is the special construction of the dehydration section where contact between the wet well gas and strong glycol occurs. This special construction, which provides both co-current and counter-current contact between the gas and the glycol has been found to result in improved removal of water vapor and reduced blow over of glycol as the gas leaves the dehydration section. In the preferred construction a dehydration stage includes a column of packing, such as steel O-rings, and two glycol spray inlets. One of the spray inlets sprays glycol into the gas stream before it passes through the packing which is kept wet by means of the other spray inlet.

This can be achieved by first passing the gas upwardly through an imperforate vertical pipe which is embedded in the packing bed with its upper end opening into a chamber located in the column above or in the packing bed. The first glycol spray inlet is located in the chamber and the chamber is in communication with an outer vertical pipe which surrounds the first pipe. The gas and glycol droplets flow co-currently downwardly from the chamber through the annulus between the inner and outer pipes, and then radially outward through apertures in the outer pipe into the lower portion of the packing bed. The gas flows upwardly through the bed and then into the lower end of the inner pipe of the next higher dehydration stage, if such stage is present. Wet glycol is removed from the packing bed at a level above the lower end of the bed, with the result that a body of glycol resides in the bed below the glycol removal point. Co-current contact between gas and liquid occurs in the column below the glycol outlet, and counter-current contact occurs in the column above the glycol outlet.

BRIEF DESCRIPTION OF THE DRAWING

FIG. 2 is a flow sheet illustrating the various fluid flows in the system of FIG. 1;

DETAILED DESCRIPTION

Figure 1:
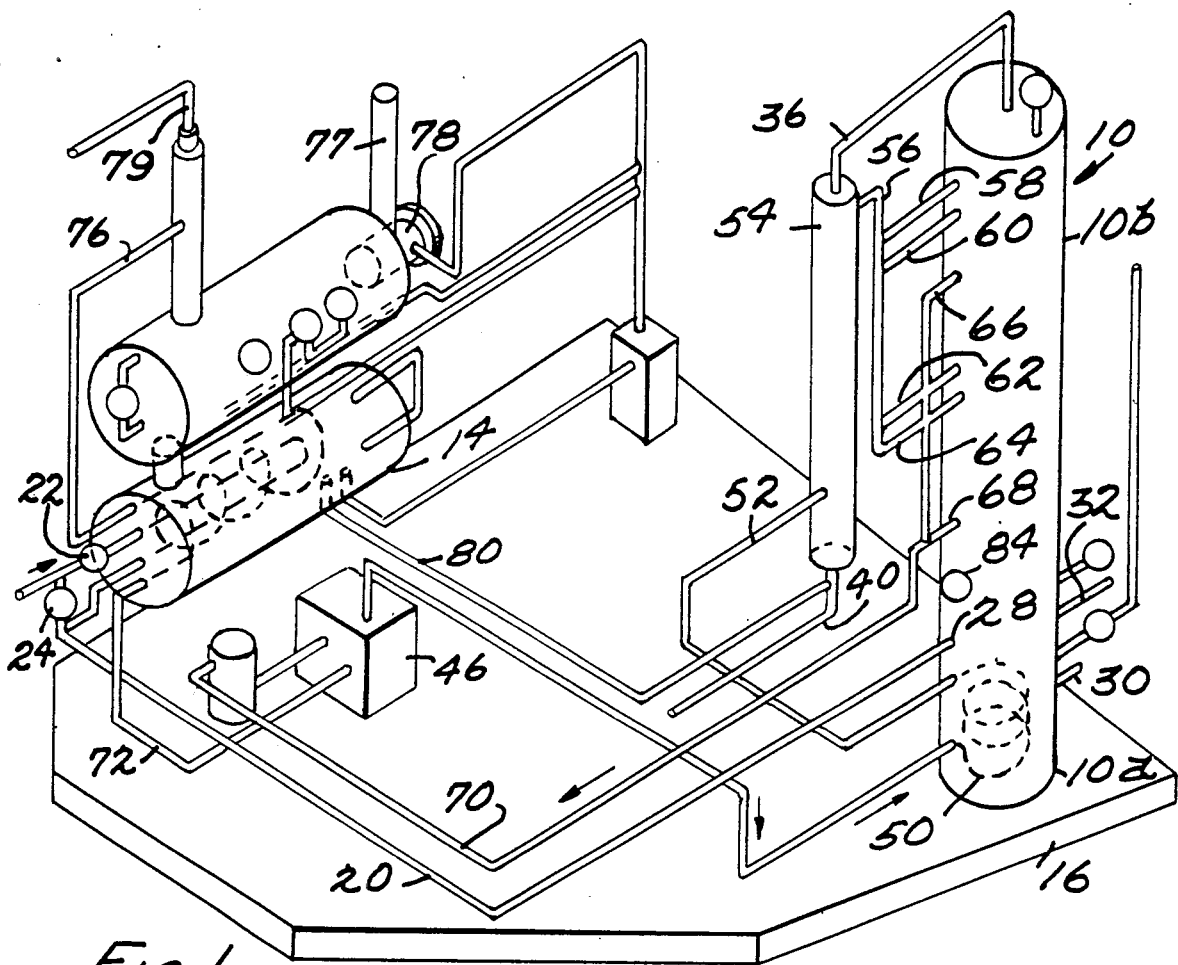
FIG. 1 is a schematic perspective view of a gas conditioning system embodying the principles of the present invention.
Figure 3:
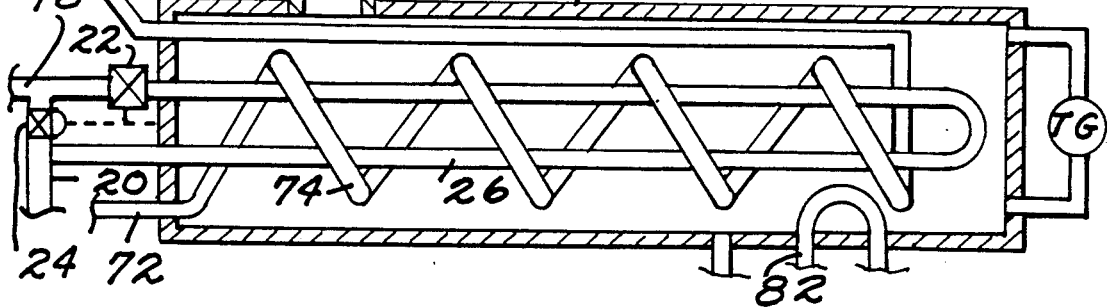
FIG. 3 is a fragmentary view, on an enlarged scale, of the reboiler and gas-heating portion of the system of FIG. 1.

The natural gas conditioning system illustrated in the drawings comprises as its major components, a combined separator-dehydrator unit 10 and a glycol reboiler 12 which includes a hot glycol storage vessel 14. The system is typically mounted on a ground-supported skid 16 which is located adjacent a natural gas well head (not shown). The reboiler 12 may be conventional and therefore is not described in detail; as is well known in the gas conditioning art a reboiler distills water vapor from a solution of water and glycol (weak glycol) thereby forming glycol containing little or no water (strong glycol), using heat provided by burning a portion of the gas from the well. The strong glycol is used in the dehydrator portion 10a of the unit 10 to absorb water vapor from the natural gas, thereby forming weak glycol which is recycled to the reboiler 12.

The strong glycol storage vessel 14, the separator-dehydrator 10 and certain of the piping and control connections within the system are special to the system and are described in full below.

Natural gas from the well head enters the system by way of a gas inlet pipe 18 and thereafter enters the separator portion 10a of the separator-dehydration unit 10 by way of a pipe 20. A valve arrangement, including valves 22 and 24, between the pipes 18 and 20 provides for passing some or all of the gas through a heat exchange loop 26 within the hot glycol storage vessel 14 before entering the pipe 20 or for passing the gas directly into the pipe 20 without passing through the heat exchange loop 26. The gas which passes through the loop 26 becomes heated, with the result that by controlling the operation of the valves 22 and 24 the temperature of the gas entering the separator portion 10a can be controlled. This has a number of advantages as will be described more in detail below.

Gas entering the separator portion 10a of the unit 10 is expanded through a choke or expansion valve 28. The operation of the separator portion 10a is conventional, except for the temperature control feature, in that liquid water and condensed hydrocarbons separate from the gas and are removed from the unit 10 after stratification, by way of a water discharge line 30 and a liquid hydrocarbon discharge line 32. The interface between the water and the liquid hydrocarbons is illustrated at 34 in FIGS. 2 and 4. Wet gas, that is gas containing water vapor, then passes upwardly to the dehydrator portion 10b of the unit, and after removal of the water vapor the resulting dry gas passes out of the upper end of the dehydrator portion 10b by way of a pipe 36, through a heat exchanger 38 and then to a dry gas discharge pipe 40.

The glycol circuit is as follows. Hot strong glycol from the reboiler 12 flows through a pipe 42 to the glycol storage vessel 14 from which it is withdrawn via pipe 44 by a pump 46 such as a conventional Kimray pump. From the pump 46 the glycol passes via a pipe 48 through a heat exchange coil 50 in the separator portion 10a of the unit 10 and then via a pipe 52 to a heat exchanger 54. The temperature of the glycol is reduced in the coil 50 by heat exchange with the contents of the separator portion 10a and is further reduced in the heat exchanger 54 by heat exchange with the dry gas from the dehydrator portion 10b. From the heat exchanger 54 the glycol flows into a header 56 from which it passes into the dehydrator portion 10b via pipes 58, 60, 62 and 64. After contact with the wet gas in the dehydrator portion 10b the glycol, now cool and weak, flows from the latter through pipes 66 and 68 to a pipe 70, then through the pump 46 to a pipe 72 which connects with a heat exchange coil 74 in the hot glycol storage vessel 14. After being preheated in the coil 74 the weak glycol flows through a pipe 76 to the reboiler 12. The reboiler 12 includes a gas-fired burner 78 which receives dry natural gas tapped through a pipe 80 from the dry gas discharge pipe 40. The fuel gas is preheated in a heat exchange coil 82 located in the hot glycol storage vessel 14 before passing to the burner 78. Flue gas is discharged to the atmosphere through a stack 77. Water vapor removed from the glycol is discharged to the atmosphere through a stack 79.

Referring more specifically to the control over the temperature of the separator portion 10a of the separator-dehydrator unit 10 provided by the present invention it will be seen from FIG. 2 that a temperature sensor 84 senses the temperature of the expanding gas in the separator portion 10a. A control line 86 from the sensor 84 provides control signals to the valves 22 and 24 which control the flow of raw natural gas either through the heat exchange loop 26 or in bypass relationship to the loop 26 before entering the separator portion 10a. When the temperature in the separator portion 10a decreases below a preselected value, the valve 22 opens and the valve 24 closes; when the separator temperature increases to a preselected value, the valve 22 closes and the valve 24 opens. Typically it is desired to maintain the temperature of the gas in the separator between about 60° F. and about 75° F. As stated previously, this temperature range achieves efficient removal of liquid water and liquid hydrocarbons. If the temperature is too low, freezing of the water at and near the point of gas expansion may occur. If the temperature is too high condensible hydrocarbons will remain in vapor form and will pass into the dehydration portion 10b and adversely affect the absorption operation. This control of the separator temperature has the further advantage of tending to stabilize the operating temperatures in the glycol circuit because the heat transfer which takes place in the dehydrator portion 10b remains relatively constant.

The components of the separator temperature control system may be conventional per se, in that the control signal produced by the sensor 84 is a fluid pressure signal and in that the valves 22 and 24 are fluid-pressure operated. The fluid is dry natural gas which may be tapped from the gas circuit by way of a line 98.

Figure 4:
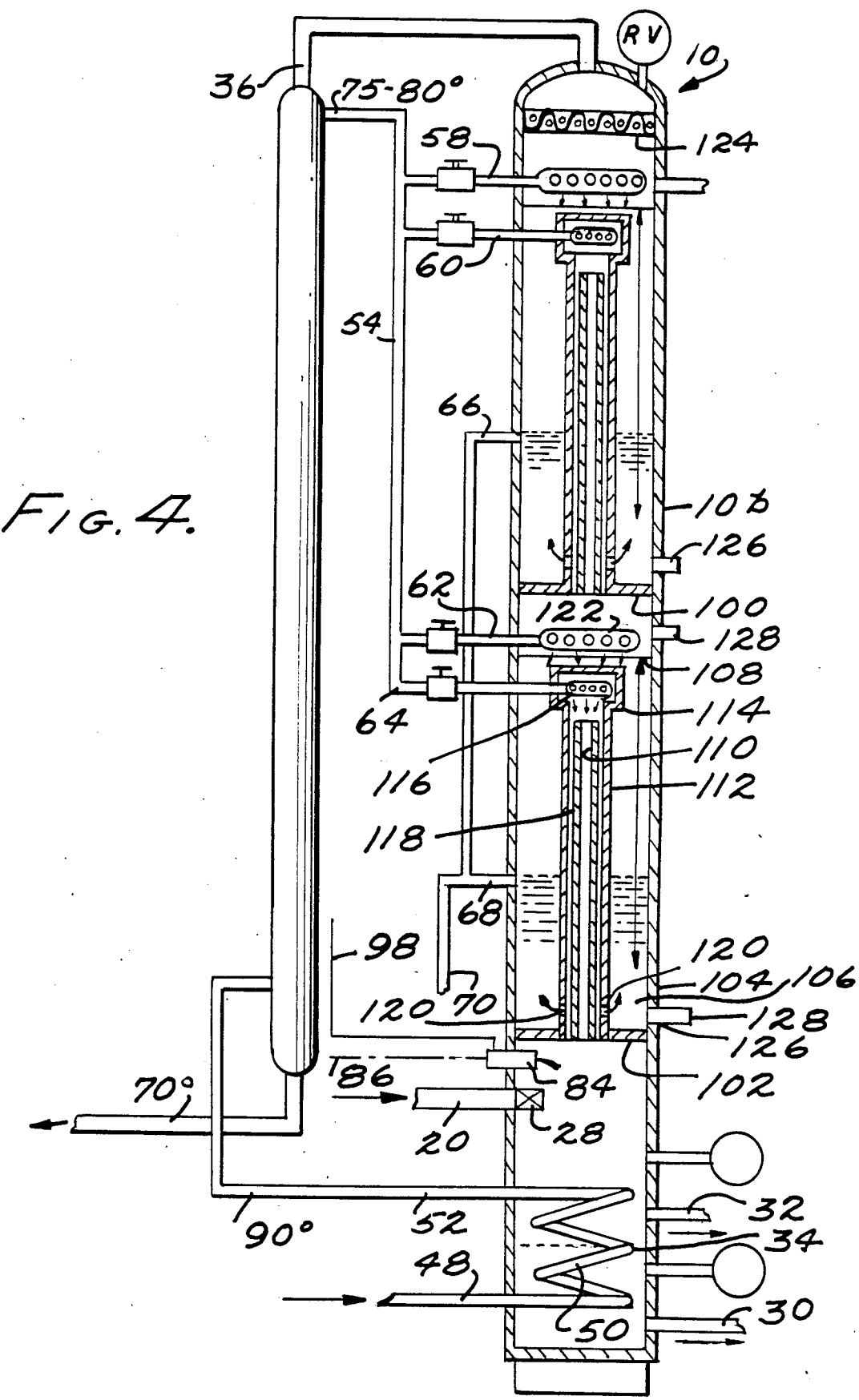
FIG. 4 is a fragmentary view of the separator-dehydration unit of the system of FIG. 1.

FIG. 4 illustrates the internal construction of the dehydration portion 10b of the unit 10. In the illustrated embodiment there are two series-connected identical stages. Each stage itself is a plural-stage gas-liquid contactor in the sense that both co-current and counter-current flows occur in each stage. The strong glycol should be about 10°-15° F. warmer than the gas. The first or lowermost stage is defined between vertically spaced-apart plates 100 and 102 which are sealed to the inner surface of the cylindrical side wall 104 of the unit 10. Supported on the upper surface of the lower plate 102 is a bed 106 of gas/liquid contact packing material such as steel rings, the bed having an upper surface 108 located below the upper plate 100. Axially located within the bed 106 are inner and outer vertical concentric pipes 110 and 112 fixed to the lower plate 102. The inner pipe 110 has an open lower end in communication with the gas space in the separator portion 10a and an open upper end residing in a chamber 114 provided at the upper end of the outer pipe 112. A spray ring 116 or other form of injector is mounted in the chamber 114 for injecting strong glycol into contact with wet gas flowing upwardly through the inner pipe 110. The resulting mixture flows downwardly in co-current contact through the annulus 118 between the inner and outer pipes 110 and 112 and then radially outward through openings 120 in the side of the outer pipe 112 so as to pass into the lower portion of the bed 106. The gas and glycol then flow up through the portion of the bed 106 in co-current contact, the glycol leaving the bed through the discharge pipe 68 which is located between the upper and lower ends of the bed 106, and the gas continuing to flow up through the upper portion of the bed 106. Additional strong glycol is introduced to the upper portion of the bed 106 by means of a spray ring 122 or other injector located in the space between the upper surface 108 of the bed 106 and the upper plate 100, this glycol also flowing out of the bed through the pipe 68. Thus in the upper portion of the bed 106 the gas and glycol flow in counter-current relationship.

The gas leaving the upper end of the bed 106 flows into the second dehydration stage which has the same construction as the first stage. From the upper end of the packed bed in the second stage, the gas passes through a mist extractor 124 and then into the pipe 36.

The side wall 104 of the dehydrator portion is provided with openings 126 which are normally closed with removable closures such as knock-off caps 128. The openings 126 are located at the lower ends of the two packed beds and slightly above the upper surfaces of the beds so that the packing may be removed and replenished when necessary. As the packing tends to become contaminated during use and must be replaced periodically, the presence of the openable and closable openings 126 simplifies the replacement operation.

The overall operation of the sytem may be summarized as follows. Raw natural gas from the wellhead (not shown), typically at a pressure up to 1200 psi and a temperature of 100°-110° F., passes either (a) through the heat exchange loop 26 so as to be heated before passing to the separator portion 10a or (b) directly to the separator portion 10a. As described previously, these flows are controlled by the valves 22 and 24 which are operated by the temperature sensor 84 in the separator portion 10a in a manner to maintain a preselected temperature range of say 60°-75° F. in the separator portion 10a. After expansion of the gas in the separator portion 10a and consequent removal of liquid water and condensed hydrocarbons the wet gas flows through the dehydrator portion 10b where water vapor is removed by contact with strong glycol. The special construction and operation of the dehydrator portion 10b effects very efficient dehydration and low glycol carry over. The resulting dry gas flows out of the upper end of the dehydrator portion through the pipe 36, through the heat exchanger 54 and then to the pipe 40 for sales or storage. Some typical gas temperatures and pressures and typical glycol temperatures in the system are shown in FIG. 2. Except for the control of the separator temperature the valves for these parameters are not critical and will vary from system to system within appropriate ranges recognized in the art.

What is claimed is:

1. In a method for conditioning natural gas from a gas well, said method including expanding the gas to separate liquid water and condensible hydrocarbons therefrom, contacting the resulting wet gas with a liquid dessicant which absorbs water vapor from the wet gas and heating the liquid dessicant to drive off water therefrom, the improvement comprising maintaining the temperature of the expanding gas within a preselected range by controllably heating the gas prior to expansion by heat exchange with heated dessicant from the dessicant-heating step in response to the temperature of the expanding gas.

2. A method as in claim 1 wherein the step of controllably heating the gas includes passing the gas in heat exchange relationship with the heated dessicant and bypassing the heat exchange relationship so as to pass unheated gas to the separating step in accordance with a preselected high temperature of the gas in the separating step.

3. In a method of conditioning natural gas: expanding the gas and removing therefrom the resulting liquid water and condensed liquid hydrocarbons and dehydrating the resulting wet gas by spraying strong liquid dessicant into a stream of the wet gas thereby forming a gas/liquid stream in which the gas and liquid are in co-current contact with each other, introducing the gas/liquid stream into the lower portion of a bed of gas-liquid contact material and passing the gas and dessicant upwardly in the bed in co-current contact, removing weak dessicant from the bed above the location at which the gas/liquid stream is introduced, introducing additional strong liquid dessicant into the upper portion of the bed and passing the thus introduced dessicant downwardly in the upper portion of the bed in counter-current contact with the gas passing upwardly from the lower portion of the bed.

4. In apparatus for conditioning natural gas from a gas well including a separator in which the gas is expanded through a choke into a separator space and from which liquid water and condensed liquid hydrocarbons are removed, a dehydrator in which wet gas from the separator is contacted with a liquid dessicant which absorbs water vapor from the wet gas, and a reboiler for heating the liquid dessicant from the dehydrator to drive off water from the dessicant: heat exchange means for heating well gas before the gas passes through said choke o said separator space; and control means responsive to the temperature in said separator space for controlling the flow of gas through said heat exchange means to thereby control the temperature in said separator space.

5. Apparatus as in claim 4 wherein said heat exchange means is arranged to pass well gas in heat exchange relationship with hot liquid dessicant from the reboiler and wherein said control means includes a temperature sensor for sensing the temperature of the gas expanding in said separator and a bypass assembly controlled by said sensor for passing at least a portion of the well gas through said heat exchanger in response to a predetermined low temperature in said separator and for bypassing said heat exchanger in response to a predetermined higher temperature in said separator.

6. Apparatus as in claim 4 including a gas-fired heater in said reboiler, a storage tank connected to said reboiler to receive hot liquid dessicant therefrom and second heat exchange means in association with liquid dessicant in said storage tank for passing warm liquid dessicant from said dehydrator in heat exchange relationship with the hot dessicant in said storage tank before the dessicant from said dehydrator passes to said reboiler, whereby the dessicant from said dehydrator is preheated and the temperature of the dessicant in said storage tank is reduced, said well-gas heat exchange means being arranged to pass the well gas in heat exchange relationship with dessicant in said storage tank thereby extracting additional heat from the dessicant in said storage tank.

7. In apparatus for conditioning natural gas from a gas well, of the type including a separator in which the gas is expanded to separate liquid water and condensible hydrocarbons therefrom; a dehydrator in which wet gas from the separator is contacted with a liquid dessicant which absorbs water vapor from the wet gas and a reboiler for heating weak liquid dessicant from the dehydrator to drive off water to form strong dessicant, an improved dehydrator having a first contacting stage comprising an inner generally vertical conduit having an open upper end and a lower end in communication with said separator so as to conduct wet gas from said separator, an outer generally vertical conduit surrounding said inner conduit, said outer conduit having a closed upper end located above the open upper end of said inner conduit and an open lower end, means for introducing strong liquid dessicant into the upper end of said outer conduit whereby the introduced dessicant and the gas issuing from the upper end of said inner conduit pass downwardly in contact with each other through said outer conduit; and a second dehydrator stage comprising a column of gas/liquid packing material surrounding said outer conduit of said first dehydrator stage and having a lower end portion in communication with the open lower end of said outer conduit so that gas and liquid dessicant issuing therefrom pass upwardly in said column of packing material, means for introducing strong liquid dessicant into the upper portion of said column of packing material and means for removing weak liquid dessicant from said column of packing material at a location intermediate the upper and lower portions of said column.

8. In a separator-dehydrator for conditioning natural gas: an elongated vessel having a separation stage in one end for expanding the gas and removing the resulting liquid water and condensed hydrocarbons; at least one dehydration stage in said vessel adjacent the separation stage for contacting the wet gas from the separation stage with strong liquid dessicant, said dehydration stage comprising conduit means for conducting wet gas from said separation stage, means for spraying strong liquid dessicant into said conduit means so as to effect contact of the gas passing therethrough with droplets of the dessicant, a bed of gas/liquid contact material in said vessel, means for passing the resulting gas-dessicant mixture into the lower portion of the bed of contact material, means for introducing additional strong liquid dessicant into the upper portion of the bed of contact material, means for removing weak dessicant from the bed at a location between the upper and lower portions of the bed and means for removing dry gas from said vessel.

9. Apparatus for conditioning natural gas from a gas well comprising: a vertically-elongated separator-dehydrator vessel having therein a lower separating space into which well gas is expanded through a choke and an upper dehydrating space in which wet gas from said separating space is passed in contact with a warm strong liquid dessicant which absorbs water vapor from the wet gas; a dessicant reboiler vessel heated by a well gas burner; a dessicant storage tank for receiving strong hot dessicant from said reboiler; first and second heat exchange means in said storage tank; means for passing weak liquid dessicant from said separator space after contact with wet gas to said reboiler via said first heat exchange means thereby extracting heat from the liquid dessicant in said storage tank; a temperature sensor in said separating space of said separator-dehydrator vessel for sensing the temperature of gas expanding in said space; means for selectively passing gas from the well either directly to said choke or through said second heat exchange means and then to said choke in response to a predetermined low temperature of gas expanding in said separator space thereby controlling the temperature of the expanding gas; and means for passing warm strong dessicant from said storage tank to said dehydrator space in said separator-dehydrator vessel.

10. Apparatus as in claim 9 wherein said dehydrator space includes a first contacting stage comprising an inner generally vertical conduit having an open upper end and a lower end in communication with said separating space so as to conduct wet gas from said separating space, an outer generally vertical conduit surrounding said inner conduit, said outer conduit having a closed upper end located above the open upper end of said inner conduit and an open lower end, said means for passing warm strong liquid dessicant introducing said dessicant into the upper end of said outer conduit whereby the introduced dessicant and the gas issuing from the upper end of said inner conduit pass downwardly in contact with each other through said outer conduit; and a second dehydrator stage comprising a column of gas/liquid packing material surrounding said outer conduit of said first dehydrator stage and having a lower end portion in communication with the open lower end of said outer-conduit so that gas and liquid dessicant issuing therefrom pass upwardly in said column of packing material, said means for passing warm strong liquid dessicant also introducing said dessicant into the upper portion of said column of packing material and means for removing weak liquid dessicant from said column of packing material at a location intermediate the upper and lower portions of said column.

11. Apparatus for conditioning natural gas from a gas well comprising: a separator in which the gas is expanded; a dehydrator in which wet gas from said separator is passed in contact with a warm strong liquid dessicant which absorbs water vapor from the wet gas; a dessicant reboiler vessel heated by a well gas burner; a dessicant storage tank for receiving strong hot dessicant from said reboiler; first and second heat exchange means in said storage tank; means for passing weak liquid dessicant from said separator after contact with wet gas to said reboiler via said first heat excahnge means thereby extracting heat from the liquid dessicant in said storage tank; and means for selectively passing gas from the well either directly to said separator or through said second heat exchange means and then to said separator thereby controlling the temperature of the expanding gas; and means for passing warm strong dessicant from said storage tank to said dehydrator.

* * * * *